(12) United States Patent
Koko et al.

(10) Patent No.: US 6,380,185 B1
(45) Date of Patent: Apr. 30, 2002

(54) N-SUBSTITUTED BENZOYL INDOLES AS ESTROGENIC AGENTS

(75) Inventors: Marci C. Koko, Wayne; John W. Ullrich, Schwenksville; Arthur A. Santilli, Havertown, all of PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/513,807

(22) Filed: Feb. 25, 2000

Related U.S. Application Data
(60) Provisional application No. 60/155,200, filed on Mar. 4, 1999.

(51) Int. Cl.[7] .................. A61K 31/55; A61K 31/535; A61K 31/445; A61K 31/40; A61K 31/405
(52) U.S. Cl. .................. 514/217.08; 514/235.2; 514/323; 514/414; 514/415; 540/602; 544/144; 546/201; 548/456; 548/491
(58) Field of Search .............. 514/217.08, 235.2, 514/323, 414, 415; 540/602; 544/144; 546/201; 548/465, 491

(56) References Cited

U.S. PATENT DOCUMENTS

| | | | |
|---|---|---|---|
| 4,943,572 A | 7/1990 | Von Angerer | 514/235.2 |
| 5,496,844 A | 3/1996 | Inai et al. | 514/415 |

FOREIGN PATENT DOCUMENTS

| | | |
|---|---|---|
| EP | 0802183 | 10/1997 |
| WO | 9310741 | 6/1993 |
| WO | 9517383 | 6/1995 |
| WO | 9603375 | 2/1996 |

OTHER PUBLICATIONS

Von Angerer, Chem. Abs., 1983, 99(7), 53886u.
Von Angerer et al., J. Med. Chem., 1987, 30, 131–136.
Von Angerer et al., J. Med. Chem., 1990, 33, 2635–2640.
Jones et al., J. Med. Chem., 1984, 27, 1057–1066.

*Primary Examiner*—Brenda Coleman
(74) *Attorney, Agent, or Firm*—Arnold S. Milowsky

(57) ABSTRACT

The present invention provides compounds of the formula:

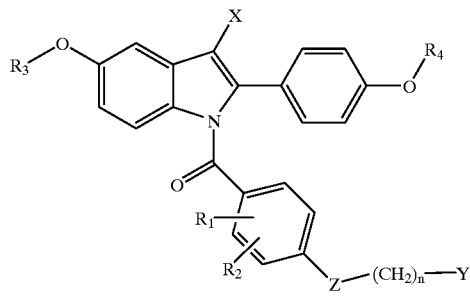

wherein $R_1$, $R_2$, $R_3$, $R_4$, X, n Y and Z, are as defined in the specification, or a pharmaceutically acceptable salt thereof, as well as pharmaceutical formulations and methods of treating or preventing disease states or syndromes which are caused or associated with an estrogen deficiency or an excess of estrogen utilizing these compounds.

9 Claims, No Drawings

N-SUBSTITUTED BENZOYL INDOLES AS ESTROGENIC AGENTS

This application claims the benefit of U.S. Provisional Application No. 60/155,200 filed Mar. 4, 1999.

The present invention relates to new N-substituted benzoyl indole compounds which are useful as estrogenic agents, as well as pharmaceutical compositions and methods of treatment utilizing these compounds.

BACKGROUND OF THE INVENTION

Estrogen replacement therapy has been well established as the treatment of choice in women for the prevention of osteoporosis. [C. Christiansen, R. Lindsay, Estrogen, Bone Loss and Preservation, Osteoporosis International, 1, 15–21 (1990)] The downside to this therapy is that when estrogen is given alone i.e. without the opposing effects of progestins, proliferative effects on the uterus may result and thereby can put the patient at risk for endometrial cancer. Although less clear, hormone replacement therapy has been implicated in increasing the incidence of breast tumor formation. Non-steroidal antiestrogen drugs such as tamoxifen have been used in the treatment of breast cancer. The drug also is known to maintain bone mass, acting as a bone-sparing estrogen agonist, however it is also an agonist in uterine tissue. A more recent antiestrogen drug, Lilly's raloxifene, is a non-steroidal antiestrogen which appears to be more tissue selective. While having the desirable property of sparing bone, it has been demonstrated to stimulate uterine growth in animal models to a lesser degree than tamoxifen. Additionally, recent clinical data reveal no endometrial hyperplasia. A review on the tissue selective action of estrogen analogs has recently appeared. [G. L. Evans and R. T. Turner, Tissue Selective Actions of Estrogen Analogs, Bone, 17, no. 4, 181S–190S (1995)].

The use of indoles as estrogen antagonists has been reported by Von Angerer, Chemical Abstracts, Vol. 99, No. 7 (1983), Abstract No. 53886u. Also, see, J. Med. Chem. 1990, 33, 2635–2640; J. Med. Chem. 1987, 30, 131–136. Also see Ger. Offen., DE 3821148 A1 891228 and WO 96/03375. These prior art compounds share some structural similarities with the present compounds, but are functionally different. For compounds containing a basic amine, there is no phenyl group to ridgidify the side chain. The reported data for these compounds indicates that they may have a weaker binding to estrogen receptor than the compounds of the present invention and the basic side chain containing compounds show some uterotrophic effect in the rat uterus.

WO A 95 17383 (Kar Bio AB) describes indole antiestrogens with long straight chains. Another related patent WO A 93 10741 describes 5-hydroxyindole with a generic descriptor incorporating other side chains.

U.S. Pat. No. 5,496,844 (Inai, et al.) teaches substituted N-indole compounds having potent antiestrogenic activity which are useful in the treatment of estrogen-dependent diseases, such as anovulatory infertility, prostatic hypertrophy, osteoporosis, breast cancer, endometrial cancer and melanoma.

Jones et al., in their article Antiestrogens. 2.[1] Structure-Activity Studies in a Series of 3-Aroyl-2-arylbenzo[b]thiophene Derivatives Leading to [6-Hydroxy-2-(4-hydroxyphenyl)benzo[b] thien-3-yl][4-[2-(1-piperidinyl)ethoxy]phenyl]methanone Hydrochloride (LY156758), a Remarkably Effective Estrogen Antagonist with Only Minimal Intrinsic Estrogenicity, J. Med. Chem. 1984, 27, 1057–1066, disclose a series of 3-aroyl-2-arylbenzo[b]thiophene derivatives which act as non-steroidal antiestrogens.

The compounds described in the present invention are mixed estrogen agonists/antagonists and have potential use in treating osteoporosis, endometriosis, prostatic hypertrophy, breast cancer and endometrial cancer.

DESCRIPTION OF THE INVENTION

The present invention provides N-substituted indoles of Formula (I):

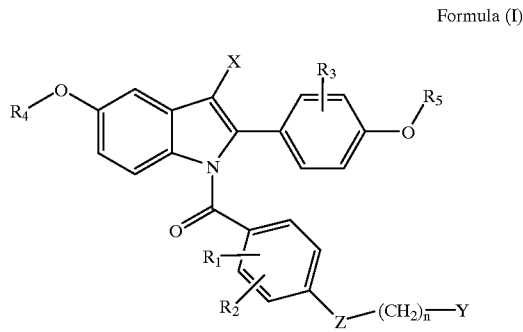

Formula (I)

wherein $R_1$, $R_2$ and $R_3$ are independently selected from hydrogen, $C_1$–$C_6$ alkyl, $C_1$–$C_6$ alkoxy, —$CF_3$, —$NO_2$, cyano, $C_1$–$C_6$ alkyl (straight chain or branched), trifluoromethyl, —OH or the $C_1$–$C_{12}$ esters (straight chain or branched) or $C_1$–$C_{12}$ alkyl ethers (straight chain or branched or cyclic) thereof, halogens, or $C_1$–$C_6$ halogenated ethers, preferably $C_1$–$C_3$ halogenated ethers, including trifluoromethyl ether and trichloromethyl ether;

$R_4$ and $R_5$ are independently selected from H or benzyl, the benzyl group being optionally substituted by $C_1$–$C_6$ alkyl, $C_1$–$C_6$ alkoxy, —$CF_3$, or halogen;

X is H, $C_1$–$C_6$ alkyl, or $CF_3$;

Z is O or S;

n is 2 or 3;

Y is selected from:

a) a moiety of the formula:

wherein R' is $C_1$–$C_6$ lower alkyl; or b) a moiety selected from the group of:

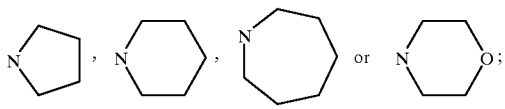

or a pharmaceutically acceptable salt thereof.

A preferred group of this invention are those compounds of Formula I wherein $R_1$, $R_2$ and $R_3$ are independently selected from hydrogen, $C_1$–$C_6$ alkyl, $C_1$–$C_6$ alkoxy, —$CF_3$, or —$NO_2$; and $R_4$, $R_5$, X, Z, n, and Y are as defined above, or a pharmaceutically acceptable salt thereof.

Another preferred group of compounds of this invention are those in which Z is oxygen and $R_1$, $R_2$, $R_3$, $R_4$ and $R_5$ are H, or a pharmaceutically acceptable salt thereof. Among the most preferred compounds of these generic and subgeneric groups are those in which Y is a piperidine ring.

This invention includes acceptable salt forms formed from the addition reaction with either inorganic or organic acids. Inorganic acids such as hydrochloric acid, hydrobromic acid, hydroiodic acid, sulfuric acid, phosphoric acid, nitric acid as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. Among the preferred salts of the compounds herein are the HCl, HBr, and acetate salts.

The compounds of the invention are partial estrogen agonists and display high affinity for the estrogen receptor. Unlike many estrogens, however, many of these compounds do not cause the increases in uterine wet weight normally associated with natural or synthetic estrogens. These compounds are antiestrogenic in the uterus and antagonize the trophic effects of estrogen agonists in uterine tissue. In addition, the compounds may be used as estrogen agonists in bone tissue. Due to the tissue selective nature of these compounds, they are useful in treating or preventing in a mammal disease states or syndromes which are caused or associated with an estrogen deficiency or an excess of estrogen.

The present compounds have the ability to behave like estrogen agonists by lowering cholesterol and preventing bone loss. These compounds are useful for treating many maladies which result from estrogen excess or deficiency including osteoporosis, prostatic hypertrophy, male pattern baldness, ovarian cancer, infertility, breast cancer, endometrial cancer, cardiovascular disease, contraception, Alzheimer's disease, cognitive decline and other CNS disorders, as well as certain cancers, including melanoma, prostrate cancer, cancers of the colon, CNS cancers, among others. Additionally, these compounds can be used for hormone replacement therapy in post-menopausal women or in other estrogen deficiency states where estrogen supplementation would be beneficial.

The compounds of this invention may also be used in methods of treatment for bone loss, which may result from an imbalance in an individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subject to the judgement of the medical practitioner involved. It is preferred that the administration of one or more of the compounds herein begin at a low dose and be increased until the desired effects are achieved.

Effective administration of these compounds may be given at an effective dose of from about 0.1 mg/day to about 1,000 mg/day. Preferably, administration will be from about 10 mg/day to about 600 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Compounds of this invention may be prepared by methods known in the art. For instance, the starting or core indole can be prepared by the general method of Scheme 1, below.

1057–1066 or as shown in Scheme 2 and coupled to the core indoles via the method of Scheme 3.

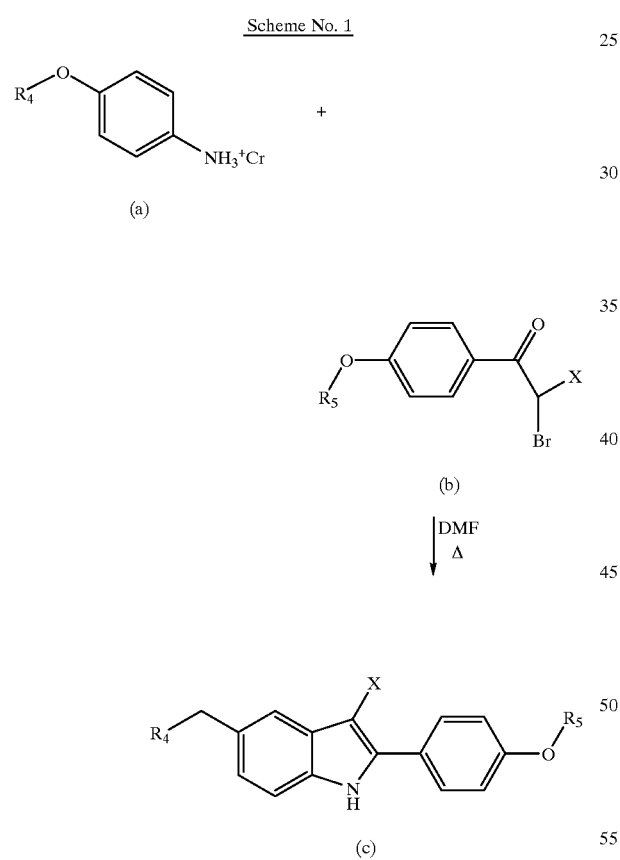

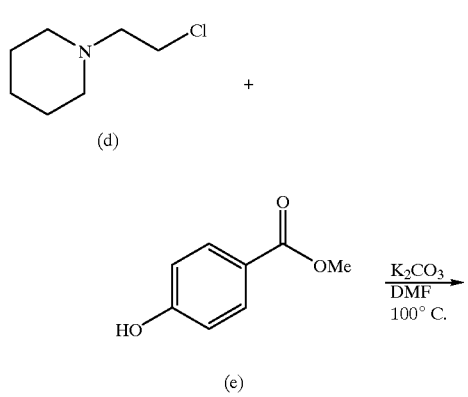

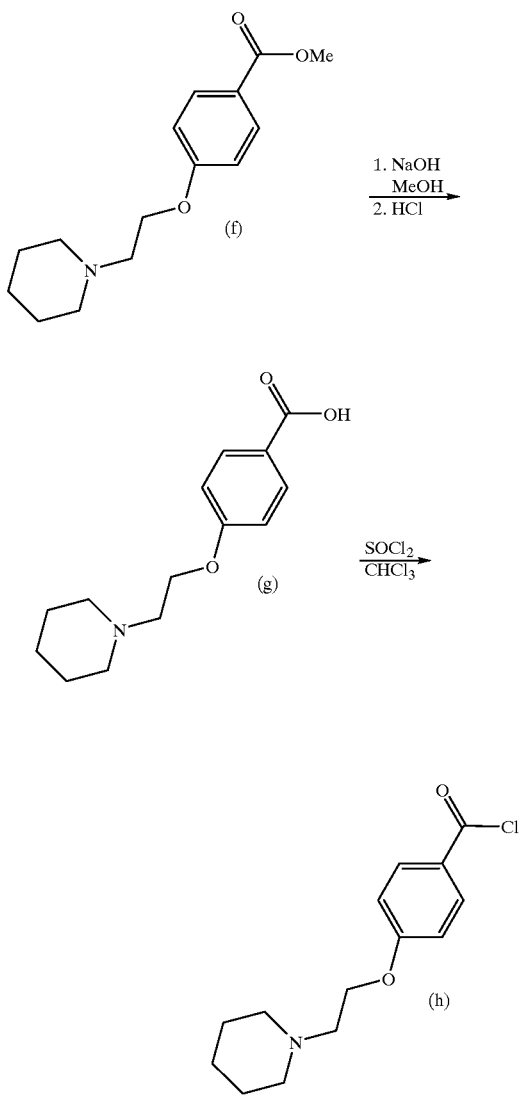

The initial indole synthesis for 5-Benzyloxy-2-(4-benzyloxy-phenyl)-3-methyl-1H-indole is accomplished by heating an appropriately substituted alpha-bromo ketone (b) with the desired aniline (a) in DMF to form the indole (c). The (aminoethoxy)benzoic acid side chains of the present compounds may be prepared by the general methods taught by Jones et al., J. Med. Chem., 1984, Vol. 27, No. 8, pp.

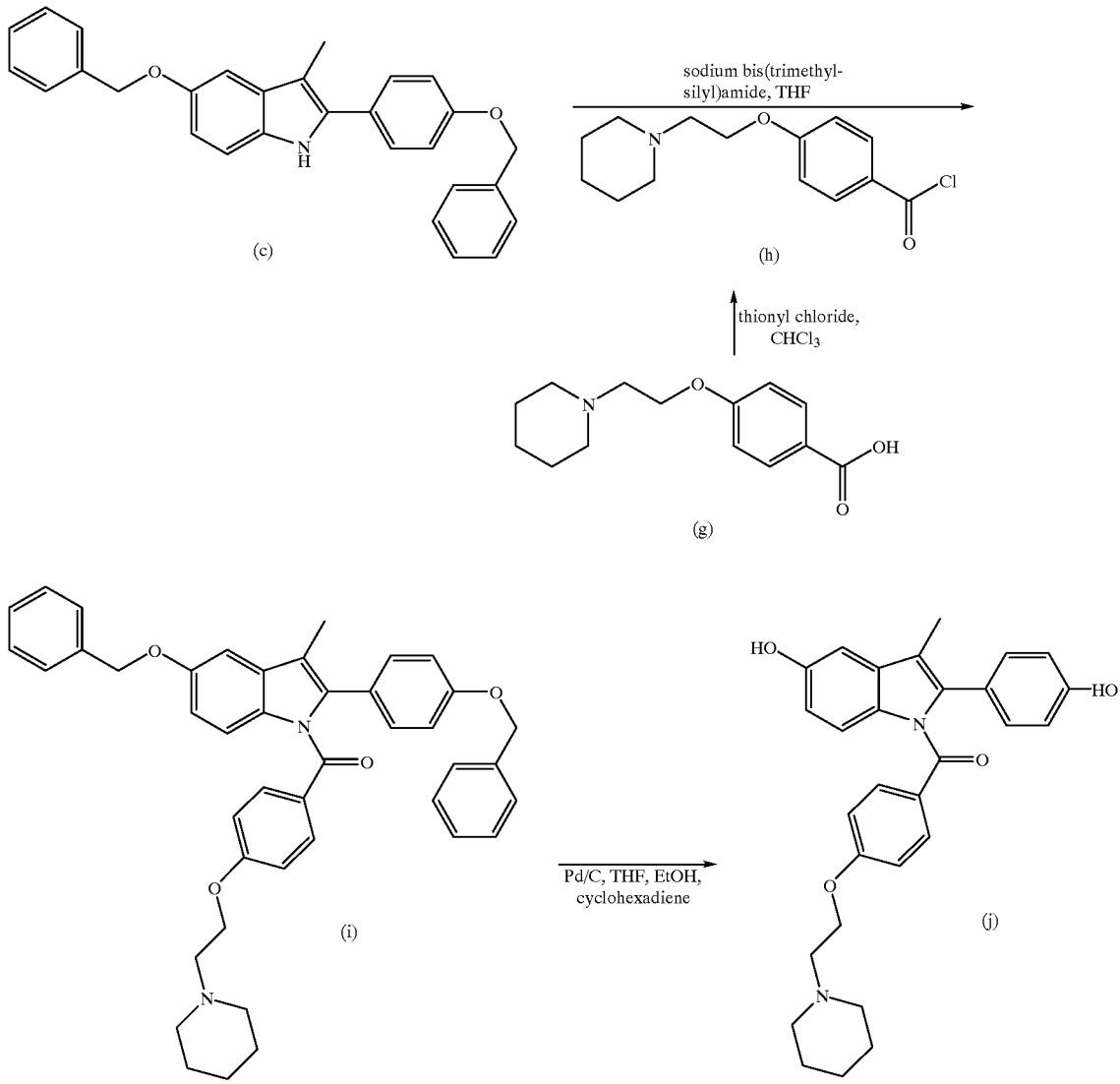

Scheme No. 3

EXAMPLE NO. 1

[5-Benzyloxy-2-(4-benzyloxy-phenyl)-3-methyl-indol-1-yl]-[4-(2-piperidin-1-yl-ethoxy)-phenyl]-methanone To a chilled (−78° C.) solution of 2.42 g (0.00577 mol) of the starting indole (c) in 60 mL of dry THF, under $N_2$, was added 2.6 g (0.00866 mol) of the acid chloride (h), and stirred at −78° C. for 20 minutes. 22 mL (0.0216 mol) of sodium bis(trimethylsilyl)amide (1.0 M solution in THF) was added dropwise to the reaction mixture and stirred at −78° C. for 30 minutes. The reaction mixture was then brought to 0° C. for 4 hours, and then to room temperature for 1 hour. 100 mL of ethyl acetate was added to the crude reaction mixture and washed with aq. $NaHCO_3$ (2×50 mL). The organic phase was collected, washed with water (2×50 mL), saturated brine, removed, dried over magnesium sulfate, filtered and evaporated to dryness in a rotary evaporator. The crude product when subjected to HPLC gave 1.25 g of yellow solid.

Mp=48–51° C.; $^1$H NMR (DMSO) 7.55–7.30 (m, 11 H), 7.24–7.16 (m, 5 H), 6.94–6.88 (m, 5 H), 5.18 (s, 2 H), 5.05 (s, 2 H), 4.09 (t, 2 H, J=5.8 Hz), 2.19 (t 2 H, J=5.8 Hz), 2.41–2.38 (m, 4 H), 2.21 (s, 3 H), 1.51–1.35 (m, 6 H); IR 3440, 2900, 1610 cm$^{-1}$; MS eI m/z 651 (M+); CHN calcd for $C_{43}H_{42}N_2O_4$ 0.25 $H_2O$.

EXAMPLE NO. 2

[5-Hydroxy-2-(4-hydroxy-phenyl)-3-methyl-indol-1-yl][4-(2-piperidin-1-yl-ethoxy)-phenyl]-methanone To a solution of 0.78 g (0.00120 mol) of [5-benzyloxy-2-(4-benzyloxy-phenyl)-3-methyl-indol-1-yl]-[4-(2-piperidin-1-yl-ethoxy)-phenyl]-methanone (described above) in 5 mL of dry THF, and 5 mL of punctilious ethanol, under $N_2$, was added 1.4 mL (0.0120 mol) of cyclohexadiene and 0.39 g (one-half the mass of the benzyloxy starting material) of 10% Pd/C, and stirred at room temperature overnight. The reaction mixture was filtered and evaporated to dryness in a rotary evaporator. 100 mL of ethyl acetate was added to the crude product. This organic phase was washed with water (2×50 mL), saturated brine, removed, dried over magnesium sulfate, filtered and evaporated to dryness in a rotary evaporator. The crude product when subjected to HPLC gave 0.30 g of pale-yellow solid.

Mp=127–130° C.; $^1$H NMR (DMSO) 9.47 (s, 1 H), 9.17 (s, 1 H), 7.48 (d, 2 H, J=8.6 Hz), 7.21 (d, 1 H, J=8.8 Hz), 7.03 (d, 2 H, J=8.4 Hz), 6.90–6.85 (m, 3 H) 6.69–6.62 (m, 3 H), 4.07 (q, 2 H, J=5.8 Hz), 2.62 (t, 2 H, J=5.8 Hz), 2.40–2.39 (m, 4 H), 2.15 (s, 3 H), 1.52–1.47 (m, 6 H); IR 3440, 2900, 1610 cm$^{-1}$; MS eI m/z 471 (M+); CHN calcd for $C_{29}H_{30}N_2O_4$ 0.5 $H_2O$.

EXAMPLE NO. 3

4-(2-Piperidin-1-yl-ethoxy)-benzoyl chloride Hydrochloride

The title compound was prepared as described by Jones, Charles D., Journal of Medicinal Chemistry, 1984, Vol. 27, No. 8, pp. 1057–1066.

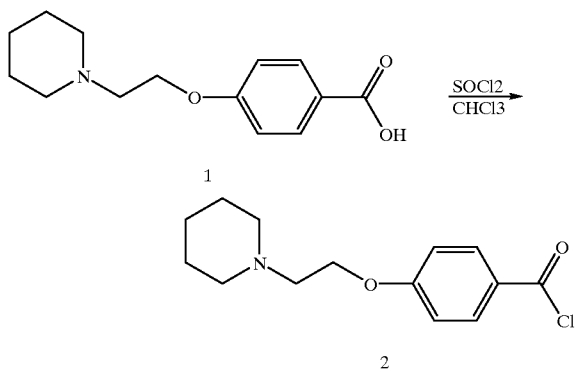

To a solution of the acid HCl salt 1 (1.0 g, 3.7 mmol) in 50 ml chloroform at room temperature, a solution of thionyl chloride (0.3 ml, 4.4 mmol) in 10 ml chloroform is added. The resulting solution is brought to 60° C. for 6 hours. The reaction mixture is then allowed to cool to room temperature and diluted with hexane. The reaction mixture is then cooled to 0° C. and the resulting acid chloride HCl salt, 2, is isolated by filtration, dried and used without purification in the acylation step.

Estrogen Receptor Binding/Competition Assay
Objective

To identify compounds that compete with 17β-estradiol for estrogen receptor (ER) binding. The widely accepted mode for estrogenic action is via its high affinity receptor protein. Compounds which demonstrate an ability to bind to the ER may then regulate physiological processes associated with estrogen action.
Procedure Receptor Preparation: CHO cells overexpressing the estrogen receptor are grown in 150 mm$^2$ dishes in DMEM+ 10% dextran coated charcoal, stripped fetal bovine serum. The plates are washed twice with PBS and once with 10 mM Tris-HCl, pH 7.4, 1 mM EDTA. Cells are harvested by scraping the surface and then the cell suspension is placed on ice. Cells are disrupted with a hand-held motorized tissue grinder using two, 10-second bursts. The crude preparation is centrifuged at 12,000×g for 20 min. followed by a 60 min spin at 100,000×g to produce a ribosome-free cytosol. The cytosol is frozen and stored at −80 deg C. Protein concentration of the cytosol is estimated using the BCA assay with BSA as the reference standard protein.

Binding Assay Conditions

The competition assay is performed in a 96-well plate (polystyrene*) which binds <2.0% of the total input [3H]-17 β-estradiol. Each data point is gathered in triplicate. 100 μg/100 μl of the receptor preparation is aliquoted per well. A saturating dose of 2.5 nM [3H]17 β-estradiol+competitor (or buffer) in a 50 μl volume is added in the preliminary competition when 100× and 500× competitor concentrations are evaluated. For an $IC_{50}$ determination, where 12 concentrations of competitor are evaluated, only 0.8 nM [3H]17 β-estradiol is used. The plate is incubated at room temperature for 2.5 h. At the end of this incubation period 150 μl of ice-cold dextran coated charcoal (5% activated charcoal coated with 0.05% 69K dextran) is added/well and the plate is immediately centrifuged at 900×g for 5 minutes at 4 deg C. 200 μl of the supernatant solution is removed for scintillation counting. Samples are counted to 2% or 10 min, whichever occurs first.

Because polystyrene absorbs a small amount of [3H]17 β-estradiol, wells containing radioactivity and cytosol, but not processed with charcoal are included to quantitate amount of available isotope. Also, wells containing radioactivity but no cytosol are processed with charcoal to estimate unremovable DPM of [3H]17 β-estradiol. Corning #25880-96 96-well plates were used because they demonstrated the least binding of estradiol of those tested.

Analysis of Results

Counts per minute (CPM) of radioactivity are automatically converted to disintegrations per minute (DPM) by the Beckman LS7500 Scintillation Counter using a set of quenched standards to generate a H# for each sample. To calculate the % of estradiol binding in the presence of 100 or 500 fold competitor the following formula is applied:

((DPM sample−DPM not removed by charcoal/(DPM estradiol− DPM not removed by charcoal))×100%=% of estradiol binding For the generation of $IC_{50}$ curves, % binding is plotted vs [compound]. $IC_{50}$'s are generated for compounds that show >10% competition at up to a 500× competitor concentration.

Reference Compounds

Various reference compounds have been evaluated and their $IC_{50}$ concentration determined. The concentration of these compounds required to displace 50% of [3H]17β-estradiol is:

estradiol: 0.08 μM tamoxifen: 4.50 μM raloxifene 0.04 μM

17α-dihydroequilin 0.15 μM

Assay Results

To demonstrate the utility of the compounds of this invention, the compound of Example No. 2 was tested against the standards tamoxifen, also named (Z)-2-[4-(1,2-Diphenyl-1-butenyl)-phenoxy]-N,N-dimethylethanamine, and raloxifene, also named [6-Hydroxy-2-(4-hydroxy-phenyl)-benzo[b]thiophene-3-yl]-[4-(2-piperidin-1-yl-ethoxy)-phenyl]-methanone. It is understood that 17β-estradiol as a standard has 100% binding in the Receptor Binding Assay.

| | Receptor Binding | | |
|---|---|---|---|
| | | Transfection Assay | |
| Compound | Assay $-IC_{50}$ | Concentration | % Control |
| Example No. 2 | $2.0 \times 10^{-7}$ M | $1 \times 10^{-6}$ M | 0 |
| | | $1 \times 10^{-6}$ M + 1 nM estradiol | 13 |
| tamoxifen | $4.5 \times 10^{-6}$ M | $1 \times 10^{-6}$ M | 0 |
| | | $1 \times 10^{-6}$ M + 1 nM estradiol | 10 |
| raloxifene | $4 \times 10^{-8}$ M | $1 \times 10^{-6}$ M | 0 |
| | | $1 \times 10^{-6}$ M + 1 nM estradiol | 0 |

What is claimed:

1. A compound of the formula:

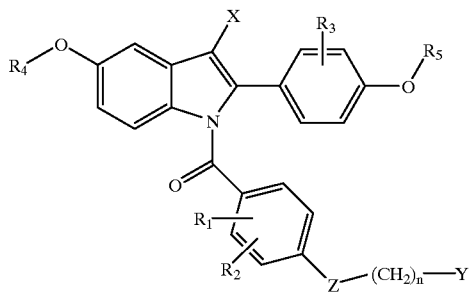

wherein $R_1$, $R_2$ and $R_3$ are independently selected from hydrogen, $C_1$–$C_6$ alkyl, $C_1$–$C_6$ alkoxy, —$CF_3$, —$NO_2$, cyano, $C_1$–$C_6$ alkyl (straight chain or branched), trifluoromethyl, —OH or the $C_1$–$C_{12}$ esters (straight chain or branched) or $C_1$–$C_{12}$ alkyl ethers (straight chain or branched or cyclic) thereof, halogen, or $C_1$–$C_6$ halogenated ethers;

$R_4$ and $R_5$ are independently selected from H or benzyl, the benzyl group being optionally substituted by $C_1$–$C_6$ alkyl, $C_1$–$C_6$ alkoxy, —$CF_3$, or halogen;

X is H, $C_1$–$C_6$ alkyl, or $CF_3$;

Z is O or S;

n is 2 or 3;

Y is selected from:
  a) a moiety of the formula:

wherein R' is $C_1$–$C_6$ lower alkyl; or b) a moiety selected from the group of:

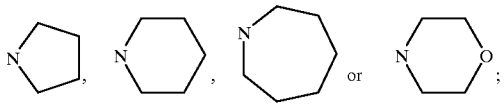

or a pharmaceutically acceptable salt thereof.

2. A compound of claim 1 wherein:

$R_1$ and $R_2$ are independently selected from hydrogen, $C_1$–$C_6$ alkyl, $C_1$–$C_6$ alkoxy, —$CF_3$, or —$NO_2$;

$R_4$ and $R_5$ are independently selected from H or benzyl, optionally substituted by $C_1$–$C_6$ alkyl, $C_1$–$C_6$ alkoxy, —$CF_3$, or halogen;

X is H, $C_1$–$C_6$ alkyl, or $CF_3$;

Z is O or S;

Y is selected from:
  a) a moiety of the formula:

wherein R' is $C_1$–$C_6$ lower alkyl; or b) a moiety selected from the group of:

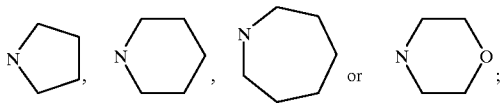

or a pharmaceutically acceptable salt thereof.

3. A compound of claim 1 wherein Z is oxygen, $R_3$ and $R_4$ are H, $R_1$ and $R_2$ are H, and X and Y are as defined in claim 1; or a pharmaceutically acceptable salt thereof.

4. A compound of claim 3 in which Y is a piperidine ring, or a pharmaceutically acceptable salt thereof.

5. A compound of claim 1 which is [5-Benzyloxy-2-(4-benzyloxy-phenyl)-3-methyl-indol-1-yl]-[4-(2-piperidin-1-yl-ethoxy)-phenyl]-methanone.

6. A compound of claim 1 which is [5-Hydroxy-2-(4-hydroxy-phenyl)-3-methyl-indol-1-yl]-[4-(2-piperidin-1-yl-ethoxy)-phenyl]-methanone, or a pharmaceutically acceptable salt thereof.

7. A method of treating bone loss in a mammal, the method comprising administering to a mammal in need thereof an effective amount of a compound of claim 1, or a pharmaceutically acceptable salt thereof.

8. A method of treating disease states or syndromes which are caused or associated with an estrogen deficiency in a mammal, the method comprising administering to a mammal in need thereof an effective amount of a compound of claim 1, or a pharmaceutically acceptable salt thereof.

9. A method of treating cardiovascular disease in a mammal, the method comprising administering to a mammal in need thereof an effective amount of a compound of claim 1, or a pharmaceutically acceptable salt thereof.

* * * * *